United States Patent
Marchioni

(10) Patent No.: US 7,087,250 B2
(45) Date of Patent: Aug. 8, 2006

(54) THERAPEUTIC COMPOSITION PROVIDING RESPIRATORY RELIEF

(76) Inventor: Artista Marchioni, 41 Aspen Way, Rolling Hills Estates, CA (US) 90274

( * ) Notice: Subject to any disclaimer, the term of this patent is extended or adjusted under 35 U.S.C. 154(b) by 46 days.

(21) Appl. No.: 10/652,051

(22) Filed: Aug. 30, 2003

(65) Prior Publication Data
US 2005/0048130 A1    Mar. 3, 2005

(51) Int. Cl.
*A01N 59/16* (2006.01)
*A01N 65/00* (2006.01)

(52) U.S. Cl. ............... 424/618; 424/757; 424/773
(58) Field of Classification Search ........ 424/618, 424/757, 773
See application file for complete search history.

(56) References Cited

U.S. PATENT DOCUMENTS 5,128,132 A * 7/1992 Parnell ................ 424/725
6,503,542 B1 * 1/2003 Sheu ................... 424/728
6,579,543 B1 * 6/2003 McClung ............. 424/728

OTHER PUBLICATIONS

Clinical Plant Tidbits (www.pshm.org/clinical_tidbits.shtml).*
Titled Herbs2000.com (www.herbs2000.com/disorders/pneumonia.htm).*
DW 1988-353804, Dec. 1988, Derwent WO, Badmajew.*
DW 2001-280848, Apr. 2001, Derwent, Bland.*
DW 2002-677207, Jun. 2002, Derwent, Kuwabara.*
DW 1999-205446, Dec. 1998, Derwent, Zhang.*

* cited by examiner

*Primary Examiner*—Susan Coe
*Assistant Examiner*—Randall Winston
(74) *Attorney, Agent, or Firm*—Karambelas & Associates

(57) ABSTRACT

A herbal therapeutic composition is provided which enhances respiration comprising coloidal silver, osha root and fresh lobelia herb. Other herbal substituents which further enhance this novel composition are disclosed including licorice root, fresh yerba santa leaf, eyebright, cats claw, rosemary, fresh ginger, and grape seed.

17 Claims, No Drawings

THERAPEUTIC COMPOSITION PROVIDING RESPIRATORY RELIEF

I. FIELD OF THE INVENTION

This invention relates to personal therapeutic compositions generally and more specifically to a composition, which enhances respiration especially in adverse environments, e.g., smog conditions. The term "smog" is generally used to mean chemical air pollution and comprises a combination of the words smoke and fog, or a contraction thereof. The primary source of smog appears to be the result of combustion of fossil fuels, commonly referred to as gasoline, in automobiles. This pollution has been known to exacerbate respiratory conditions in humans and result in many health problems.

It is known that smog may comprise many different chemical particles that result in air pollution, the severity of which is generally assessed by measuring the ground level of ozone in an area. It is know that ground level ozone is different from the ozone layer, which is found at high altitudes in the atmosphere. These smog levels depend on many factors including, but not limited to, automobile use, manufacturing, weather conditions and applicable government regulations governing air quality.

Smog is generally known to impact the lungs, and consequently, breathing and can be serious in the case of senior citizens, the young and those with preexisting lung conditions such as asthma and other pulmonary maladies. Heavy smog exposure is known to cause shortness of breath, coughing, wheezing and painful breathing in addition to watery eyes among other problems. Typically these types of symptoms usually subside or are eliminated when the person involved avoids or eliminates exposure to such environments such as, for example, remaining indoors during heavy smog conditions.

As above recited these symptoms can be quite serious in those with preexisting health problems such as in the case for asthmatics where, for example, scientific studies have shown that the number of lung infections, hospital visits and hospitalizations go up with increasing smog levels in those with these conditions. Not surprisingly, general lung functions have also been shown to decline with increasing air pollution. It has also been observed that an increased number of deaths in those with prior heart or lung disease occurs in regions with heavy smog levels.

Further studies have shown that well trained athletes have shown a reduced capacity for exercise in areas with high levels of smog. There is also a further concern that air pollution may lead to the development of new diseases, such as new cases of asthma or emphysema. Although not established, a link between lung cancer and certain air pollutants in strongly suspected and likely, though more research in needed in this area.

Heavy smog may also result from catastrophic occurrences such as volcanic eruptions, earthquakes, explosions and the like. For example, in addition to the horrible disaster experienced at the World Trade Center, breathing conditions were near impossible for substantial periods of time after the attack.

Naturally occurring high levels of smog occur more on sunny, hot and humid days. Experience has shown that peak smog levels are often experienced during morning and afternoon rush hour periods when automobile emissions are at their highest levels. Smog is not restricted, as previously believed, to large cities and industrial areas. It also has been found to have appreciable impact in rural as well as urban areas. Classic smog as currently understood producing polluting air is visibly observed to be the well-known characteristic hazy appearance of the air, sometimes turning rusty in appearance during very high levels of smog episodes.

II. PRIOR ART

Various prior art, preventative measures and aids have been employed to alleviate the respiratory distress experienced from smog as described above. The simplest, but perhaps the most impractical approach is to remove the person from the environment to one that is relatively smog free. For example, Hawaii is known to have some of the cleanest air in the nation with Honolulu ranking among the top 25 cities with the least amount of ozone pollution according to the American Lung Association.

Staying indoors with electronic air filters and other air filtering devices is extremely restrictive and likewise impractical as a solution. Various respiratory aids have been employed, e.g., smog masks or conventional gas masks adapted to particularly address smog conditions. Various air filters and breathing devices have been employed including those that provide pure or diluted oxygen, all of which have obvious restrictions and generally present an impractical solution to this problem.

Various methods and compositions for the treatment of pathologies associated with respiratory diseases such as asthma and inflammatory responses to polluted air have provided a multitude of pharmaceuticals for treatment of the symptoms of same. These pharmaceuticals, however, present their own set of side effects and related problems resulting from their use.

Though there have been solutions proposed including those recited above relating to filtering devices, masking devices, pharmaceuticals and physically eliminating or removing those impacted by the atmosphere with varying degrees of success, dreadful conditions sometimes even involving life threatening situations continue to persist and grow as smog continues to be a problem. These potentially devastating changes including those relating to personality, family life problems, diminished work performance, irritability, impotence, insomnia, memory loss, etc. as the subject undergoes loss of breathing repeatedly during sleep continue to be a major problem.

Thus, there is a continuing demonstrated need to aid respiration for humans in conditions which include exposure to smog and other occurrences which cause difficulty in respiration.

III. OBJECTS OF THE INVENTION

An object of this invention is to provide a novel, naturally occurring composition comprising herbal components to aid respiration, devoid of the above noted deficiencies.

Still another object of this invention is to provide a novel composition, which promotes respiratory efficiency.

Still another object of this invention is to provide a composition, which promotes respiration and results in no deleterious side effects.

Yet still another object of this invention is to provide an improved therapeutic composition which promotes the body's immunity to respiratory elements.

IV. SUMMARY OF THE INVENTION

These and other objects of the instant invention are accomplished generally speaking by providing a therapeutic composition comprising herbal substituents and more specifically a herbal composition comprising colloidal silver, osha root, and fresh lobelia herb. These substituents may be employed in any suitable concentration. Typical concentrations include colloidal silver 1–3%, osha root 55–75% and fresh lobelia 20–40%. Preferable results are obtained when these three substituents are combined in the following weight percentages: colloidal silver about 2%, osha root about 65% and fresh lobelia about 33%. Colloidal silver is known to be an effective natural antibiotic. Although any suitable colloidal silver material may be employed, it is preferred to employ high quality colloidal silver containing small particles approximately $1000^{th}$ of a micron employing a true electrocolloidal process. These colloidal solutions are found to remain stable in increasing concentrations of silver. Osha root has enhanced antibacterial action and promotes proper lung and bronchial action; fresh lobelia has been found to enhance stress reduction. The unique herbal composition as recited above is found to have far superior therapeutic effects on the entire respiratory system as opposed to the collective additive effects of each of the three components. This unique therapeutic herbal composition may be further enhanced by adding licorice root. Licorice root has been found to enhance reduction or elimination of mucous and improved adrenal action. A typical herbal composition would be employed in the following concentration ranges: colloidal silver about 1–2%, osha root about 40–50%, fresh lobelia herb about 15–30%, licorice root about 15–30%. It is likewise found that further enhancement may be obtained by adding fresh yerba santa leaf which has been found to enhance the drying of mucosal tissue when secretions are excessive. Typical concentrations of this five substituent herbal therapeutic composition include colloidal silver 0.6–2%, osha root 25–45%, fresh lobelia 10–25%, licorice root 10–25%, fresh yerba santa leaf 15–35%.

Still further enhancements may be obtained by employing additionally the eyebright herb which is known to enhance the reduction of allergic response, for example, hay fever and overactive immune systems. A typical six herbal substituent composition containing eyebright would include colloidal silver about 0.5–1.5% by weight, osha root about 20–40% by weight, fresh lobelia about 10–20% by weight, fresh licorice root about 10–20% by weight, fresh yerba santa leaf about 10–30% by weight, and eyebright herb about 10–30% by weight.

In addition, it is found that further enhancements and therapeutic effects to the core three component herbal composition may be realized by further adding cats claw bark which is known to enhance stress reduction and inflammation, rosemary leaf which is a known antioxidant and increases circulation, and fresh ginger root which enhances anti-inflammatory action and improves circulation, in addition to grape seed which provides enhanced antioxidant action in addition to enhanced immune response.

A highly preferable composition embodying the three substituent core composition and others as recited above could include colloidal silver at about 0.4–1.2% by weight, osha root at about 15–20% by weight, fresh lobelia at about 5–15% by weight, licorice root at about 5–15% by weight, fresh yerba santa leaf at about 10–20% by weight, eyebright at about 10–20% by weight, and cats claw, rosemary and fresh ginger at about 1½–4½% by weight, with grape seed being employed at about ½–1½% by weight. A particularly preferred composition which is found to be most effective in smoggy areas is found to have the following composition: colloidal silver about 0.85%, osha root about 25%, fresh lobelia about 12½%, licorice root about 12½%, fresh yerba santa leaf about 19%, eyebright at about 19%, cats claw at about 3%, rosemary at about 3%, fresh ginger at about 3%, and grape seed at about 1.3%. It should be noted that peppermint spirits may be added in very small amounts to provide a more pleasing taste to this unique herbal composition.

Although these herbal substituents may be combined in any suitable manner to effect respiratory relief, the following ranges of composition for each of the substituents has been found to be preferable in application: fresh osha root 10–30%, eyebright herb 5–20%, fresh yerba santa leaf 5–20%, licorice root 2–20%, fresh lobelia herb 2–20%, cats claw bark 0.5–5%, rosemary leaf 0.5–5%, fresh ginger root 0.5–5%, green tea leaf 1–10%, peppermint spirits 0.05–0.2%, grape seed extract 1–4% and colloidal silver 0.02–0.15%.

Various solvents may be employed to provide a solution of these herbal substituents as well as various extraction techniques to provide the preferred concentrations. Any suitable solvent may be employed in providing the herbal substituents of the instant inventions. Typical solvents include water and alcohol among others.

Any suitable method of extraction may be employed in providing the herbal substituent composition of the instant invention. Typical extractions include those using grain alcohol solvents among other alcohols and conventional liquids used in solvent extractions.

Although the herbal substituents of the therapeutic respiratory composition of the instant invention may be combined in any suitable ratio including those recited above, the following working example has been found to produce optimal results when using this composition.

A composition of 930 milligrams per milliliter is produced employing any suitable solvent extraction technique to provide fresh osha root in a concentration of 22% by weight or approximately 205 milligrams per milliliter; eyebright herb at 16.5% by weight or approximately 153 milligrams per milliliter; fresh yerba santa leaf at 16.5% by weight or approximately 153 milligrams per milliliter; licorice root at 11% by weight or approximately 102 milligrams per milliliter; fresh lobelia herb at 11% by weight or approximately 102 milligrams per milliliter; cats claw bark at 2.7% by weight or approximately 25 milligrams per milliliter; rosemary leaf at 2.7% by weight or approximately 25 milligrams per milliliter; fresh ginger root at 2.7% by weight or approximately 25 milligrams per milliliter; green tea leaf at about 4.7% by weight or approximately 44 milligrams per milliliter; peppermint spirits at about 0.12% by weight or approximately 1.1 milligrams per milliliter; grape seed extract at 0.08% by weight or approximately 2.5 milligrams per milliliter; and colloidal silver at approximately 30 parts per million silver or about 0.00279 milligrams per milliliter.

In addition to alleviating the adverse symptoms resulting from smog, for example in Los Angeles, recently named the smoggiest city in the United States, additional advantages may be employed for support of the respiratory system employing the liquid composition of the instant invention. This herbal composition has been found to enhance the immune system in alleviating the affects of colds, flu, allergies, asthma, bronchitis and environmental irritation to respiratory tissues.

In addition the commercial incarnation of this herbal composition referred to as SMOG CHECK® SILVER RESERVE has been found to benefit smokers, athletes and those who suffer from altitude sickness as it enhances the ability of the lung to employ oxygen and has been found to be safe and effective for long term use. This product is provided in handy bottled form including an administering device normally in eye dropper form or spray and is to be taken typically before enduring any exposure to or episode occurring from adverse respiratory conditions.

A practical application for use of this composition is suggested during airplane flights of any duration to boost or enhance the immune system from attack by airborne irritants.

In addition to those benefits listed above, this novel composition has been found to be an aid to those with sinus congestion, lung congestion, bacterial or viral infections, stress symptoms, inflammation and circulatory problems. This therapeutic respiratory composition has been found to enhance antibacterial action, antiviral action, antiallergenic action, improve oxygenation, provide antihistamine action, act as an antioxidant, enhance stress alleviation, provide enhanced anti-inflammatory action, reduce coughing and mucous production, increase circulation and enhance antimicrobio action.

Although each of the individual substituents have shown characteristics as follows, any one of them may be substituted with a suitable substituent in a suitable concentration to provide the same properties: osha root has enhanced antibacterial action and promotes proper lung and bronchial action; eyebright enhances the reduction of allergic response in, for example, hay fever and overactive immune systems; yerba santa has been found to enhance the drying of mucosal tissue when secretions are excessive; licorice root has been found to enhance reduction or elimination of mucous and improved adrenal action; lobelia has been found to enhance stress reduction; green tea has been found to enhance antioxidants and enhance the immune system; cats claw bark has been found to enhance stress reduction and inflammation; rosemary leaf has been found to enhance antioxidant action and increase circulation; ginger root has been found to enhance anti-inflammatory action and improve circulation; peppermint has been found to enhance alleviation of sinusitis; and grape seed has provided enhanced antioxidant action in addition to enhanced immune response.

While the present invention has been particularly described with respect to preferred concentrations of preferred substituents, it will be understood that the invention is not limited to these particular concentrations and substituents described in the preferred embodiments. For example, the optimal combination of this therapeutic composition may be varied accordingly by substituting for the above substituents, substitute substituents in suitable concentrations that possess the same or similar properties as outlined above to obtain the same or similar results as above recited. It is intended to cover all alternatives, modifications, and equivalents as may be included within the spirit and scope of the invention defined by the appended claims.

In addition, other substituents may be employed in the instant invention as claimed with similar results. In particular, the scope of the invention is intended to include, for example, adding in suitable concentrations the flavoring substituents to obtain a different or more pleasing taste for varying palates. In addition, other substituents may be added to enhance solubility and appearance of these compositions, in addition to other substituents which provide further synergy to these herbal compositions.

What is claimed is:

1. A therapeutic respiratory herbal composition comprising colloidal silver, osha root and fresh lobelia.

2. The composition as defined in claim 1 wherein said colloidal silver is in a concentration of about 1–3%, osha root is in a concentration of about 55–75%, and fresh lobelia is in a concentration of about 20–40%.

3. A therapeutic respiratory herbal composition comprising colloidal silver at about 2%, osha root at about 65%, and fresh lobelia at about 33%.

4. The composition as defined in claim 1 further comprising licorice root.

5. The composition as defined in claim 4 wherein said colloidal silver is in a concentration of about 1–2%, osha root is in a concentration of about 40–50%, fresh lobelia is in a concentration of about 15–30%, and licorice root is in a concentration of about 15–30%.

6. A therapeutic respiratory herbal composition comprising colloidal silver at about 1.6%, osha root at about 50%, fresh lobelia at about 25%, and licorice root at about 25%.

7. The composition as defined in claim 4 further comprising fresh yerba santa leaf.

8. The composition as defined in claim 7 wherein said colloidal silver is in a concentration of about 0.6–2%, osha root is in a concentration of about 25–45%, fresh lobelia is in a concentration of about 10–25%, licorice root is in a concentration of about 10–25%, and fresh yerba santa leaf is in a concentration of about 15–35%.

9. A therapeutic respiratory herbal composition comprising colloidal silver at about 1.2%, osha root at about 36%, fresh lobelia at about 18%, licorice root at about 18%, and fresh yerba santa leaf at about 27%.

10. The composition as defined in claim 7 further comprising eyebright herb.

11. The composition as defined in claim 10 wherein said colloidal silver is in a concentration of about 0.5–1.5% by weight, osha root is in a concentration of about 20–40% by weight, fresh lobelia is in a concentration of about 10–20% by weight, fresh licorice root is in a concentration of about 10–20% by weight, fresh yerba santa leaf is in a concentration of about 10–30% by weight, and eyebright herb is in a concentration of about 10–30% by weight.

12. A therapeutic respiratory herbal composition comprising colloidal silver at about 0.95%, osha root at about 28%, fresh lobelia at about 14%, licorice root at about 14%, fresh yerba santa leaf at about 21%, and eyebright herb at about 21%.

13. The composition as defined in claim 10 further comprising rosemary.

14. The composition as defined in claim 13 wherein said colloidal silver is in a concentration of about 0.5–1.5%, osha root is in a concentration of about 20–30%, fresh lobelia is in a concentration of about 5–20%, licorice root is in a concentration of about 5–20%, fresh yerba santa leaf is in a concentration of about 10–30%, eyebright herb is in a concentration of about 10–30%, and rosemary is in a concentration of about 2–4%.

15. The composition as defined in claim 13 further comprising fresh ginger.

16. The composition as defined in claim 15 wherein said colloidal silver is at about 0.4–1.2%, osha root is at about 15–35%, fresh lobelia is at about 5–20%, licorice root is at about 5–20%, fresh yerba santa leaf is at about 10–30%, eyebright herb is at about at about 2–4%, and further comprising cats claw at about 2–4%.

17. A therapeutic respiratory herbal composition comprising colloidal silver at about less than 1%, osha root at about 25%, fresh lobelia at about 13%, licorice root at about 13%, fresh yerba santa leaf at about 20%, eyebright herb at about 20%, cats claw at about 3%, rosemary at about 3%, and fresh ginger at about 3%.

* * * * *